United States Patent [19]

Bauer et al.

[11] 4,235,826
[45] Nov. 25, 1980

[54] ESTERS OF ISOCAMPHYL-GUAIACOL, PROCESS FOR THEIR PREPARATION AND THEIR USE FOR THE PREPARATION OF 3-[ISOCAMPH-5-YL]-CYCLOHEXANOL

[75] Inventors: Kurt Bauer; Gerd-Karl Lange, both of Holzminden, Fed. Rep. of Germany

[73] Assignee: Bayer Aktiengesellschaft, Leverkusen, Fed. Rep. of Germany

[21] Appl. No.: 71,430

[22] Filed: Aug. 30, 1979

[30] Foreign Application Priority Data

Apr. 28, 1979 [DE] Fed. Rep. of Germany ....... 2917360

[51] Int. Cl.³ .................... C07F 9/11; C07F 9/12; C07C 143/02
[52] U.S. Cl. .................. 260/951; 260/456 P; 568/632; 568/734; 568/820
[58] Field of Search ........................... 260/951, 456 P

[56] References Cited

U.S. PATENT DOCUMENTS

| 2,023,551 | 12/1935 | Rosenzweig | 260/951 |
| 2,194,724 | 3/1940 | Rosenzweig | 260/951 |
| 3,510,544 | 5/1970 | Allais et al. | 260/951 |

OTHER PUBLICATIONS

Aul'chenko et al., "Chem. Abstracts", Vol. 68 (1968), p. 3878.

Primary Examiner—Joseph E. Evans
Attorney, Agent, or Firm—Sprung, Felfe, Horn, Lynch & Kramer

[57] ABSTRACT

The invention concerns new [isocamph-5-yl]-guaiacyl esters of the formula

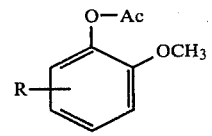

in which R represents an isocamph-5-yl radical located in the 2-position or 4-position relative to the OAc group and Ac represents a $C_1$–$C_4$-alkylsulphonyl or di-($C_1$–$C_4$-alkyl)-phosphoryl radical; a process for their preparation and their use for the preparation of 3-[isocamph-5-yl]-cyclo-hexanol which is an important constituent of sandal compound.

2 Claims, No Drawings

ESTERS OF ISOCAMPHYL-GUAIACOL, PROCESS FOR THEIR PREPARATION AND THEIR USE FOR THE PREPARATION OF 3-[ISOCAMPH-5-YL]-CYCLOHEXANOL

The invention relates to [isocamph-5-yl]-guaiacyl esters of the formula

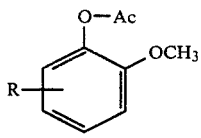 (I)

in which
R represents an isocamph-5-yl radical located in the 2-position or 4-position relative to the OAc group and
Ac represents a $C_1-C_4$-alkylsulphonyl or di-$(C_1-C_4$-alkyl)-phosphoryl radical.

The invention also relates to a process for the preparation of the esters of the formula (I). The process is characterised in that 2- or 4-[isocamph-5-yl]-guaiacol is reacted with an acid chloride of the formula AcCl (II)

in which Ac has the meaning indicated under formula (I), in the presence of an acid-binding agent.

The invention also relates to the use of the esters of the formula (I) for the preparation of 3-[isocamph-5-yl]-cyclohexanol.

$C_1-C_4$-alkyl radicals which may be mentioned are the n-propyl, i-propyl and n-butyl radicals and in particular the methyl and alkyl radical.

Preferred esters of the formula (I) are O,O-diethyl O-6-[isocamph-5-yl]-guaiacyl phosphate and in particular O,O-diethyl O-4-[isocamph-5-yl]-guaiacyl phosphate.

In order to prepare the esters, according to the invention, of the formula (I), 6- or 4-[isocamph-5-yl]-guaiacol is reacted with a $C_1-C_4$-alkylsulphonic acid chloride or a di-$(C_1-C_4$-alkyl)-phosphoric acid chloride in the presence of acid-binding agents. Isocamph-5-yl-guaiacol and the acid chloride are advantageously used in a molar ratio of 1:1-5 and preferably 1:1-1.5.

Acid-binding agents which can be used are preferably nitrogen bases, especially triethylamine and pyridine. The nitrogen bases can at the same time serve as the solvent, if they are used in an amount in excess of the amount required to bind the acid formed. However, the acylation can also be carried out in the presence of other solvents which are inert under the reaction conditions, such as benzene, toluene, acetone, diethyl ether or dioxane.

The acylation is advantageously carried out at 0° to 50° C. and preferably at 5° to 20° C.

For the preparation of the dialkyl phosphates, it has proved particularly advantageous to prepare the phosphoric acid chlorides in situ from carbon tetrachloride and the corresponding dialkyl phosphites. The isocamph-5-yl-guaiacol is dissolved in at least the equivalent amount of carbon tetrachloride. The dialkyl phosphite and trialkylamine are then added successively in an amount of 1 to 5 mols and preferably 1 to 1.1 mols per mol of isocamph-5-yl-guaiacol. Excess carbon tetrachloride can serve as the solvent. However, other chlorinated hydrocarbons, for example methylene chloride, chloroform, trichloroethylene or dichloroethylene, can also be added as solvents.

The esters according to the invention are in general obtained from their preparation in a form which is already so pure that they can be further processed direct without purification.

For further processing to 3-[isocamph-5-yl]-cyclohexanol, the esters, according to the invention, of the formula (I) are first split reductively to give 3-[isocamph-5-yl]-anisole.

The alkylsulphonates are split reductively by catalytic hydrogenation in the presence of an acid-binding agent. The hydrogenation can be carried out under normal pressure or under an elevated pressure of up to 10 atmospheres. Preferably, the hydrogenation is carried out under normal pressure. The catalysts used are finely divided noble metals, such as palladium, rhodium or ruthenium, preferably palladium, which have been applied to supports, such as charcoal. For the hydrogenation, the catalysts are employed in an amount of 0.05 to 2% by weight and preferably 0.5 to 1.5% by weight of noble metal, based on the weight of the alkylsulphonate.

In order to bind the alkylsulphonic acid formed during the hydrogenation, at least 1 mol of acid-binding agent, preferably a nitrogen base such as triethylamine or pyridine, is added. Excess nitrogen base can at the same time also serve as the solvent. However, other solvents which are inert under the reaction conditions, for example alcohols such as methanol, can also be used. The reduction is preferably carried out at room temperature.

The dialkyl phosphates are split reductively by treatment with solutions of alkali metals, such as lithium, sodium or potassium, in liquid ammonia. The alkali metals are employed in amounts of at least 2 to 4 mols and preferably 2.5 to 3 mols per mol of dialkyl phosphate. Liquid ammonia is used in an amount of 1 to 10 parts by weight and preferably 1.5 to 4 parts by weight, per part by weight of dialkyl phosphate. It has proved advantageous to add the phosphate, dissolved in diethyl ether, dropwise to a solution of the alkali metal in ammonia. Splitting of the dialkyl phosphates is carried out at −20° to −80° C. and preferably −40° to −50° C., and at a temperature above −35° C. the reaction must be carried out under pressure.

After splitting of the dialkyl phosphates has ended, an electron-capturing agent, for example sodium benzoate, is added in order to prevent formation of dihydro compounds. The alkali metal amide formed is then decomposed by adding ammonium chloride.

The 3-[isocamph-5-yl]-anisole obtained from the reductive splitting of the esters, according to the invention, of the formula (I), is converted by the process described in C.A. 68, (1968), 39823 z, by heating for several hours at 180° to 220° C. in molten pyridine hydrochloride, to 3-[isocamph-5-yl]-phenol and this is hydrogenated with hydrogen in the presence of a noble metal catalyst to give 3-[isocamph-5-yl]-cyclohexanol.

The esters, according to the invention, of the formula (I) are valuable intermediate products for the preparation of 3-[isocamph-5-yl]-cyclohexanol, which is an important constituent of sandal compound. With the aid of these esters, 3-[isocamph-5-yl]-cyclohexanol can be prepared in a considerably more economic manner than by the processes previously known.

The 2,4-dinitrophenyl ethers of 6- and 4-[isocamph-5-yl]-guaiacol proposed in C.A. 68, (1968), 39823 z as intermediate products for the preparation of 3-[isocamph-5-yl]-cyclohexanol yield 3-[isocamph-5-yl]-phenol, which is the final precursor in the preparation of 3-[isocamph-5-yl]-cyclohexanol, only in about 50% yield, based on 4-[isocamph-5-yl]-guaiacol. With the aid of the esters, according to the invention, of the formula (I), on the other hand, 3-[isocamph-5-yl]-phenol is obtained in up to 86% yield, based on 4-[isocamph-5-yl]-guaiacol. Moreover, the esters according to the invention are so much less expensive than the 2,4-dinitrophenyl ethers, for the preparation of which 2,4-dinitrofluorobenzene, which is not readily accessible and is expensive, is required, that there is no comparison between the two costs.

The process proposed in German Auslegeschrift No. (German Published Specification) 1,223,482 for the preparation of 3-[isocamph-5-yl]-cyclohexanol is even less economical than the process described in C.A. 68, (1968), 39823 z. It uses terpenylphenols as the starting materials and these are converted in a complicated multi-stage reaction via terpenyl methyl ketones to 3-[isocamph-5-yl]-cyclohex-2-en-1-one, which is then hydrogenated to 3-[isocamph-5-yl]-cyclohexanol. With this process the yield is not even 20%, based on the terpenyl phenol used as the starting material.

EXAMPLE 1

130 g (0.5 mol) of 4-[isocamph-5-yl]-guaiacol are dissolved in 43.5 g (0.55 mol) of pyridine, with warming. 63 g (0.55 mol) of methanesulphonyl chloride are added dropwise to this solution in the course of 30 minutes, whilst stirring and cooling, at a rate such that the internal temperature does not exceed 15° to 20° C. The reaction mixture is kept at 5° to 10° C. for 12 hours; 100 ml of ether and 100 ml of water are then added. The organic phase is separated off, washed with dilute hydrochloric acid and then dried and freed from solvent. Residue: 178 g.

The crude product is purified by reprecipitating from ether/petroleum ether (boiling point 30° to 40° C.). 139 g of 4-[isocamph-5-yl]-guaiacyl methanesulphonate crystallise out at −20° C.

On concentrating the mother liquor and seeding, a further 3 g of ester are obtained:

Total yield of ester: 142 g (=84% of theory); melting point: 65° C.

EXAMPLE 2

240 g (1 mol) of 4-[isocamph-5-yl]-guaiacol are dissolved in 260 ml of carbon tetrachloride. 151.8 g (1.1 mols) of diethyl phosphite are added dropwise at 20° C., whilst stirring. 113 g (1.1 mols) of triethylamine are then added dropwise, with extensive cooling. After stirring for about 5 hours at room temperature, the reaction mixture is washed with dilute hydrochloric acid and then with dilute sodium hydroxide solution. The organic phase is separated off, dried and freed from solvent.

Yield: 400 g (=100% of theory) of O,O-diethyl O-4-[isocamph-5-yl]-guaiacyl phosphate; Boiling point: 160° C./0.2 mm Hg.

EXAMPLE 3

120 g (0.35 mol) of 4-[isocamph-5-yl]-guaiacyl methanesulphonate (prepared according to Example 1) are dissolved in 800 ml of methanol. After adding 36 g (0.355 mol) of triethylamine and 12 g of 5% strength palladium-on-charcoal, the solution is hydrogenated with hydrogen under a pressure of one atmosphere. After about 6 hours, when 75% of the theoretically required amount of hydrogen has been taken up, a further 12 g of 5% strength palladium- on-charcaol are added and the hydrogenation is continued until no further hydrogen is taken up.

After filtering off the catalyst, the filtrate is concentrated to dryness. The residue is dissolved in ether. The ether solution is washed in order to remove the salts. After distilling off the ether, the residue is distilled.

Yield: 74 g (=86.7% of theory) of 3-[isocamph-5-yl]-anisole; boiling point: 160° C./1 mm Hg.

EXAMPLE 4

A solution of 1,500 g of O,O-diethyl O-4-[isocamph-5-yl]-guaiacyl phosphate (prepared according to Example 2) in 1,500 ml of diethyl ether is added slowly dropwise at −40° C. to a solution of 200 g of sodium in 4 l of liquid ammonia, whilst stirring. Towards the end of the reaction a further 20 g of sodium are added. Subsequently, first 120 g of sodium benzoate and then 350 g of ammonium chloride are added successively to the deep blue reaction solution. The ammonia is then allowed to evaporate, the residue is taken up in toluene and the toluene solution is washed with water. The toluene is stripped off in vacuo and the residue is distilled.

Yield: 840 g (=90.8% of theory) of 3-[isocamph-5-yl]-anisole; Boiling point: 131° to 139° C./0.7 mm Hg.

EXAMPLE 5

2,300 g (9.4 mols) of 3-[isocamph-5-yl]-anisole are introduced at 130° C. into 3,260 g (58.2 mols) of molten pyridine hydrochloride, whilst stirring. After adding 300 ml of glacial acetic acid, the mixture is heated at 190° C. for 3 hours. After cooling, the reaction mixture is added to water and the resulting mixture is extracted with toluene. The toluene solutions are combined and freed from toluene. The residue which remains is distilled.

Yield: 2,072 g (=95.6% of theory) of 3-[isocamph-5-yl]-phenol; Boiling point: 142° C./0.6 mm Hg.

EXAMPLE 6

690 g (3 mols) of 3-[isocamph-5-yl]-phenol are dissolved in 360 ml of methanol and hydrogenated at 140° C. in the presence of 34 g of ruthenium catalyst (5% ruthenium-on-aluminum oxide) under a hydrogen pressure of 200 atmospheres. After 3 hours the absorption of hydrogen has ceased. The catalyst is filtered off and the filtrate is freed from the solvent. The residue is distilled.

Yield: 686.5 g (=97% of theory) of 3-[isocamph-5-yl]-cyclohexanol (mixture of cis and trans isomers); Boiling point: 130° to 135° C./0.2 mm Hg.

What is claimed is:

1. [Isocamph-5-yl]-guaiacyl esters of the formula

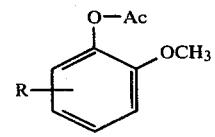

wherein
R is an isocamph-5-yl radical in the 2-position or 4-position relative to the OAc group and Ac is a $C_1$–$C_4$-alkylsulphonyl or di-($C_1$–$C_4$-alkyl)-phosphoryl radical.

2. O,O-Diethyl O-4-[isocamph-5-yl]-guaiacyl phosphate.